(12) United States Patent
Wang et al.

(10) Patent No.: US 11,102,428 B2
(45) Date of Patent: *Aug. 24, 2021

(54) SINGLE IMAGE SENSOR FOR CAPTURING MIXED STRUCTURED-LIGHT IMAGES AND REGULAR IMAGES

(71) Applicant: CAPSO VISION, Inc., Saratoga, CA (US)

(72) Inventors: Kang-Huai Wang, Saratoga, CA (US); Yi Xu, Menlo Park, CA (US); Gordon C. Wilson, San Francisco, CA (US); Chenyu Wu, Sunnyvale, CA (US)

(73) Assignee: CAPSOVISION INC, Saratoga, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/563,458

(22) Filed: Sep. 6, 2019

(65) Prior Publication Data

US 2020/0007802 A1 Jan. 2, 2020

Related U.S. Application Data

(62) Division of application No. 15/871,991, filed on Jan. 16, 2018, now Pat. No. 10,447,950, which is a
(Continued)

(51) Int. Cl.
*H04N 7/18* (2006.01)
*H04N 5/355* (2011.01)
(Continued)

(52) U.S. Cl.
CPC ..... *H04N 5/35581* (2013.01); *A61B 1/00009* (2013.01); *A61B 1/041* (2013.01);
(Continued)

(58) Field of Classification Search
CPC ............. H04N 5/35581; H04N 13/271; H04N 5/3537; H04N 5/35572; H04N 13/286;
(Continued)

(56) References Cited

U.S. PATENT DOCUMENTS 6,469,289 B1 10/2002 Scott-Thomas
6,977,685 B1 12/2005 Acosta-Serafini
(Continued)

*Primary Examiner* — Shan E Elahi
(74) *Attorney, Agent, or Firm* — Blairtech Solution LLC

(57) ABSTRACT

An integrated image sensor for capturing a mixed structured-light image and regular image using an integrated image sensor are disclosed. The integrated image sensor comprises a pixel array, one or more output circuits, one or more analog-to-digital converters, and one or more timing and control circuits. The timing and control circuits are arranged to perform a set of actions including capturing a regular image and a structured-light image. According to the present invention, the structured-light image captured before or after the regular image is used to derive depth or shape information for the regular image. An endoscope based on the above integrated image sensor is also disclosed. The endoscope may comprises a capsule housing adapted to be swallowed, where the components of integrated image sensor, a structured light source and anon-structured light source are enclosed and sealed in the capsule housing.

14 Claims, 10 Drawing Sheets

Related U.S. Application Data division of application No. 14/884,788, filed on Oct. 16, 2015, now Pat. No. 9,936,115.

(51) Int. Cl.

| | |
|---|---|
| *H04N 13/286* | (2018.01) |
| *H04N 13/296* | (2018.01) |
| *G01B 11/25* | (2006.01) |
| *H04N 13/271* | (2018.01) |
| *A61B 1/04* | (2006.01) |
| *H04N 5/353* | (2011.01) |
| *A61B 1/00* | (2006.01) |
| *A61B 1/06* | (2006.01) |
| *H04N 5/369* | (2011.01) |
| *G02B 23/24* | (2006.01) |
| *H04N 5/378* | (2011.01) |
| *H04N 5/225* | (2006.01) |

(52) U.S. Cl.
CPC .............. *A61B 1/06* (2013.01); *G01B 11/2513* (2013.01); *G02B 23/2415* (2013.01); *G02B 23/2484* (2013.01); *H04N 5/3535* (2013.01); *H04N 5/3537* (2013.01); *H04N 5/3559* (2013.01); *H04N 5/35572* (2013.01); *H04N 5/369* (2013.01); *H04N 5/378* (2013.01); *H04N 13/271* (2018.05); *H04N 13/286* (2018.05); *H04N 13/296* (2018.05); *H04N 2005/2255* (2013.01)

(58) Field of Classification Search
CPC .. H04N 13/296; H04N 5/3535; H04N 5/3559; H04N 5/378; H04N 9/045; H04N 2005/2255; G01B 11/2513; A61B 1/041; A61B 1/00009; A61B 1/06; G02B 23/2415; G02B 23/2484
USPC .......................................................... 348/45
See application file for complete search history.

(56) References Cited

U.S. PATENT DOCUMENTS

| | | |
|---|---|---|
| 7,983,458 B2 | 7/2011 | Wang |
| 8,369,458 B2 | 2/2013 | Wong et al. |
| 2004/0190085 A1* | 9/2004 | Silverbrook ........ G06F 3/03545 358/474 |
| 2004/0190092 A1* | 9/2004 | Silverbrook ....... H04N 1/00376 358/539 |
| 2006/0113459 A1 | 6/2006 | Yang |
| 2006/0268153 A1 | 11/2006 | Rice |
| 2012/0188560 A1 | 7/2012 | Bendall |
| 2014/0098224 A1 | 4/2014 | Zhang |
| 2014/0267007 A1 | 9/2014 | Capps et al. |
| 2014/0285821 A1 | 9/2014 | Regelsberger et al. |
| 2014/0347498 A1* | 11/2014 | Solhusvik ............ H04N 17/002 348/187 |
| 2015/0097108 A1 | 4/2015 | Bshay |

* cited by examiner

Ramp up voltage waveform for regular image

Ramp up voltage waveform for image with structure light

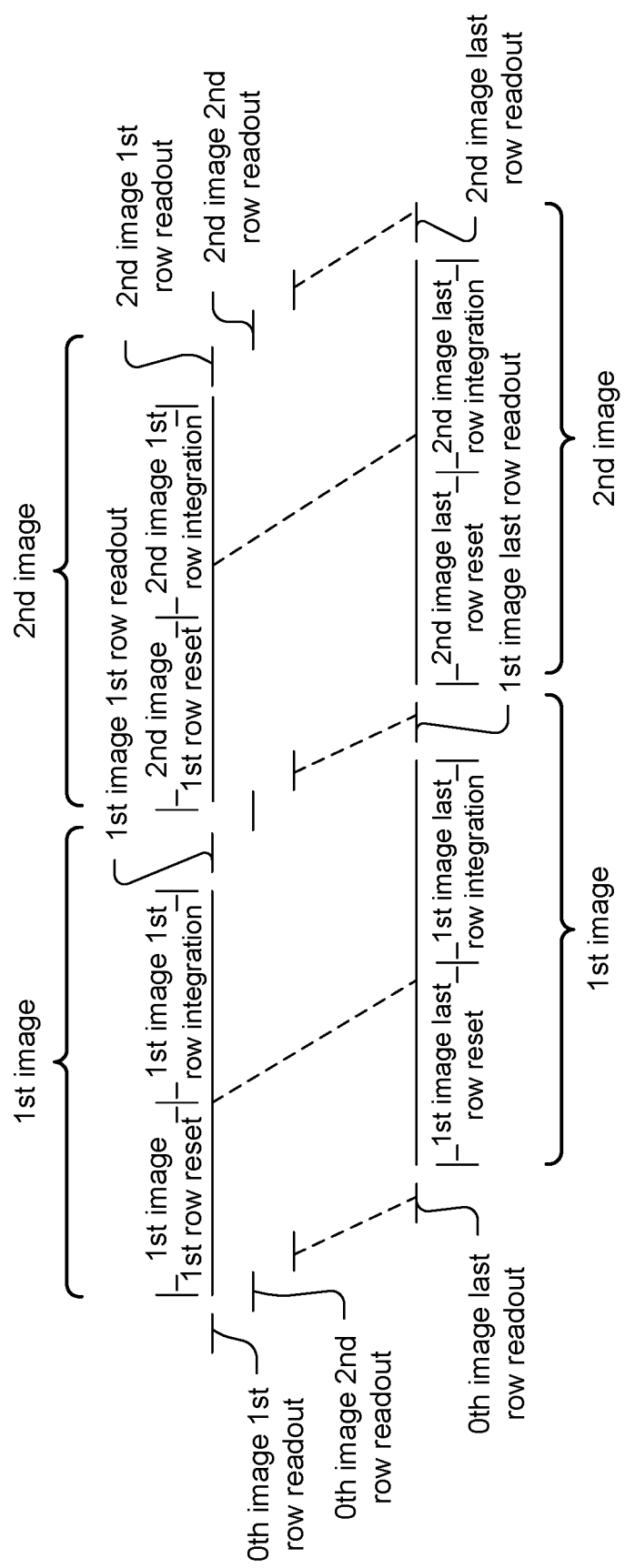
Fig. 4.1

SINGLE IMAGE SENSOR FOR CAPTURING MIXED STRUCTURED-LIGHT IMAGES AND REGULAR IMAGES

CROSS REFERENCES

The present application is a divisional application of and claims the priority to U.S. Non-provisional application Ser. No. 15/871,991, filed on Jan. 16, 2018, which is a divisional application of and claims the priority to U.S. Non-provisional application Ser. No. 14/884,788, filed on Oct. 16, 2015, now patented as U.S. Pat. No. 9,936,151 on Apr. 3, 2018. The U.S. Non-Provisional Applications are incorporated by reference in their entireties.

FIELD OF THE INVENTION

The present invention relates to a single image sensor capable of capturing structured-light images and regular image, where the structured-light image is used to derive depth or shape information related to the corresponding regular image.

BACKGROUND AND RELATED ART

Devices for imaging body cavities or passages in vivo are known in the art and include endoscopes and autonomous encapsulated cameras. Endoscopes are flexible or rigid tubes that pass into the body through an orifice or surgical opening, typically into the esophagus via the mouth or into the colon via the rectum. An image is formed at the distal end using a lens and transmitted to the proximal end, outside the body, either by a lens-relay system or by a coherent fiber-optic bundle. A conceptually similar instrument might record an image electronically at the distal end, for example using a CCD or CMOS array, and transfer the image data as an electrical signal to the proximal end through a cable. Endoscopes allow a physician control over the field of view and are well-accepted diagnostic tools.

Capsule endoscope is an alternative in vivo endoscope developed in recent years. For capsule endoscope, a camera is housed in a swallowable capsule, along with a radio transmitter for transmitting data, primarily comprising images recorded by the digital camera, to a base-station receiver or transceiver and data recorder outside the body. The capsule may also include a radio receiver for receiving instructions or other data from a base-station transmitter. Instead of radio-frequency transmission, lower-frequency electromagnetic signals may be used. Power may be supplied inductively from an external inductor to an internal inductor within the capsule or from a battery within the capsule.

An autonomous capsule camera system with on-board data storage was disclosed in the U.S. Pat. No. 7,983,458, entitled "In Vivo Autonomous Camera with On-Board Data Storage or Digital Wireless Transmission in Regulatory Approved Band," granted on Jul. 19, 2011. The capsule camera with on-board storage archives the captured images in on-board non-volatile memory. The capsule camera is retrieved upon its exiting from the human body. The images stored in the non-volatile memory of the retrieved capsule camera are then accessed through an output port on in the capsule camera.

While the two-dimensional images captured by the endoscopes have been shown useful for diagnosis, it is desirable to be able to capture gastrointestinal (GI) tract images with depth information (i.e., three-dimensional (3D) images) to improve the accuracy of diagnosis or to ease the diagnosis process. In the field of 3D imaging, 3D images may be captured using a regular camera for the texture information in the scene and a separate depth camera (e.g. Time of Flight camera) for the depth information of the scene in the field of view. The 3D images may also be captured using multiple cameras, where multiple cameras are often used in a planar configuration to capture a scene from different view angles. Then, point correspondence is established among multiple views for 3D triangulation. Nevertheless, these multi-camera systems may not be easily adapted to the GI tract environment, where the space is very limited. In the past twenty years, a structured light technology has been developed to derive the depth or shape of objects in the scene using a single camera. In the structured light system, a light source, often a projector is used to project known geometric pattern(s) onto objects in the scene. A regular camera can be used to capture images with and without the projected patterns. The images captured with the structured light can be used to derive the shapes associated with the objects in the scene. The depth or shape information is then used with regular images, which are captured with non-structured floodlit light, to create 3D textured model of the objects. The structured light technology has been well known in the field. For example, in "*Structured-light 3D surface imaging: a tutorial*" (Geng, in *Advances in Optics and Photonics*, Vol. 3, Issue 2, pp. 128-160, Mar. 31, 2011), structured light technology using various structured light patterns are described and the corresponding performances are compared. In another example, various design, calibration and implement issues are described in "3-D Computer Vision Using Structured Light: Design, Calibration and Implementation Issues" (DePiero et al., *Advances in Computers*, Volume 43, Jan. 1, 1996, pages 243-278). Accordingly, the details of the structured light technology are not repeated here.

While the structured light technology may be more suitable for 3D imaging of the GI tract than other technologies, there are still issues with the intended application for GI tract. For example, most of the structured light applications are intended for stationary object. Therefore, there is no object movement between the captured structured-light image and the regular image. Nevertheless, in the capsule camera application for GI tract imaging, both the capsule camera and the GI parts (e.g. small intestines and colons) may be moving. Therefore, there will be relative movement between the structured-light image and the regular image if they are captured consecutively. Furthermore, the capsule camera application is a very power-sensitive environment. The use of structured light will consume system power in addition to capturing the regular images. Besides, if one image with structured light is taken after each regular image, the useful frame rate will be dropped to half. If the same frame rate of regular images is maintained, the system would have to capture images at twice the regular frame rate and consume twice the power in image capture. Accordingly, it is desirable to develop technology for structured light application in the GI tract that can overcome these issues mentioned here.

BRIEF SUMMARY OF THE INVENTION

An integrated image sensor for capturing a mixed structured-light image and regular image using an integrated image sensor are disclosed. The integrated image sensor comprises a pixel array being responsive to light energy received by the pixel array to produce pixel signals having a voltage level depending on the light energy received by the pixel array; one or more output circuits coupled to the pixel array to access the pixel signals produced by the pixel array; one or more analog-to-digital converters having a first dynamic range and a second dynamic range; and one or more timing and control circuits coupled to the pixel array, said one or more output circuits, said one or more analog-to-digital converters or a combination thereof. The timing and control circuits are arranged to capture, by the pixel array, a structured-light image formed on a common image plane during a first frame period by applying first reset signals to the pixel array to reset rows of pixels of the pixel array, exposing the rows of pixels of the pixel array to first illumination from a structured light source to cause first analog signals from the rows of pixels and converting the first analog signals from the rows of pixels of the pixel array into first digital outputs for the structured-light image using one or more analog-to-digital converters; capture, by the pixel array, a first regular image formed on the common image plane during a second frame period by applying second reset signals to the pixel array to reset the rows of pixels of the pixel array, exposing the rows of pixels to second illumination from a non-structured light source to cause second analog signals from the rows of pixels, and converting the second analog signals from the rows of pixels into second digital outputs for the first regular image using said one or more analog-to-digital converters; capture, by the pixel array, a second regular image formed on the common image plane during a third frame period by applying third reset signals to the pixel array to reset the rows of pixels of the pixel array, exposing the rows of pixels to the second illumination from the non-structured light source to cause third analog signals from the rows of pixels, and converting the third analog signals from the rows of pixels into third digital outputs for the second regular image using said one or more analog-to-digital converters; and combine the second digital outputs and the third digital outputs to form a combined regular image. The structured-light image is captured between the first regular image and the second regular image to derive depth or shape information for the combined regular image.

An endoscope based on the above integrated image sensor is also disclosed. The endoscope further comprises a structured light source and a non-structured light source, which may be coupled to the timing and control circuits.

A camera system based on the above integrated image sensor is also disclosed. The camera further comprises a structured light source and a non-structured light source, which may be coupled to the timing and control circuits.

BRIEF DESCRIPTION OF THE DRAWINGS

FIG. 4A illustrates an exemplary timing chart for capturing two regular images.

DETAILED DESCRIPTION OF THE INVENTION

Figure 1:
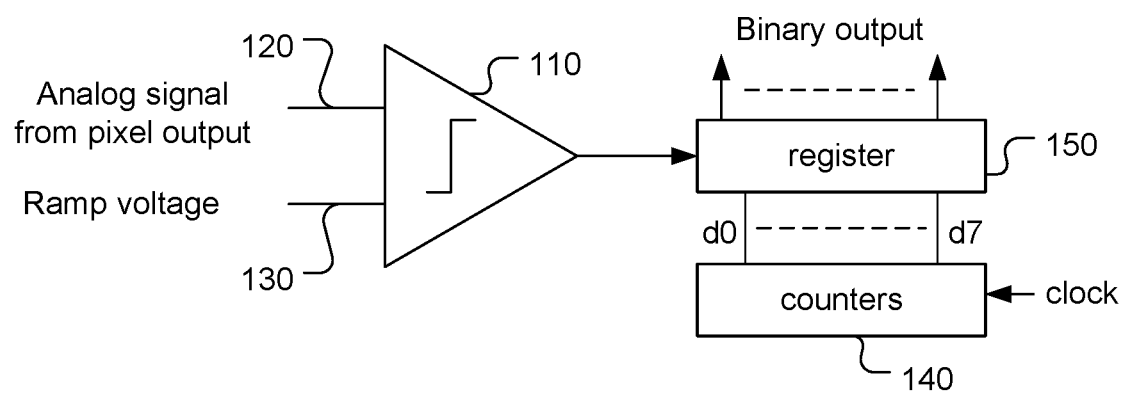
FIG. 1 illustrates exemplary analog-to-digital converter with 8-bit dynamic range.

It will be readily understood that the components of the present invention, as generally described and illustrated in the figures herein, may be arranged and designed in a wide variety of different configurations. Thus, the following more detailed description of the embodiments of the systems and methods of the present invention, as represented in the figures, is not intended to limit the scope of the invention, as claimed, but is merely representative of selected embodiments of the invention. References throughout this specification to "one embodiment," "an embodiment," or similar language mean that a particular feature, structure, or characteristic described in connection with the embodiment may be included in at least one embodiment of the present invention. Thus, appearances of the phrases "in one embodiment" or "in an embodiment" in various places throughout this specification are not necessarily all referring to the same embodiment.

Furthermore, the described features, structures, or characteristics may be combined in any suitable manner in one or more embodiments. One skilled in the relevant art will recognize, however, that the invention can be practiced without one or more of the specific details, or with other methods, components, etc. In other instances, well-known structures, or operations are not shown or described in detail to avoid obscuring aspects of the invention. The illustrated embodiments of the invention will be best understood by reference to the drawings, wherein like parts are designated by like numerals throughout. The following description is intended only by way of example, and simply illustrates certain selected embodiments of apparatus and methods that are consistent with the invention as claimed herein.

Endoscopes are normally inserted into the human body through a natural opening such as the mouth or anus. Therefore, endoscopes are preferred to be small sizes so as to be minimally invasive. To derive or capture the depth or shape information while capturing live images or videos of the GI tract with endoscopes, it is crucial to maintain the small-size form factor. Besides, with the small size and the capability to capture depth information along with corresponding images or video, such camera also finds its applications in other applications requiring compact size, such as a wearable devices.

One technique that may capture depth information is to use a color filter placed on top of selected sensor pixels with the passband reasonably narrow and capture the color information and depth information simultaneously. The environment light sources with spectrum in the filter passband will cause negligible amount of energy projected onto the sensor. For the case of RGB pixels, a fourth type of pixels may be added to capture light with the spectrum in the passband of the filter placed on top of these pixels. Then, the structured light that has the spectrum substantially in the passband can be projected onto the scene. However this approach will reduce the spatial resolution of the images or video captured using such image sensor.

Another technique is to obtain the depth information as well as 3D topology by projecting structured light patterns that are visible in the RGB sensors. However the real time image and/or video will be confounded by the structured light superimposed on it. This invention describes methods to use a single camera to achieve depth information by using the structured light approach while taking images or real time video using the camera.

As mentioned before, a conventional structured light approach with a single camera would incur several drawbacks. For example, the camera with a frame rate of 30 frames per second may be used. A conventional approach would take live video with interleaved images corresponding to images with and without the structured light. One issue is that the depth information is 1/30 second away from corresponding images to be viewed. If there is any movement in the scene, the depth information may not accurately represent the 3D topology of the corresponding images at 1/30 second away. In addition, the effective frame rate for the video to be viewed is dropped to 15 frames per second in this example.

In some video applications, the frame rate is crucial for the intended application. For example, a high frame-rate camera with frame rate in the 100's per second or more is required to capture video of fast moving objects such as a travelling bullet. In this case, the use of structured light would cut the frame rate to half and may hinder the intended application. For a capsule camera, the video for the gastrointestinal (GI) tract is normally a few frames per second and the camera could be operating at twice the original frame rate to compensate the reduction of effective frame rate due to capturing structured-light images. However, it would result in twice as much power consumption, which is not desirable in the power-limited capsule environment.

Each frame rate has a corresponding frame period. During the frame period, the sensor will spend a subset of the frame period for accumulating charges emitted in response to incidental light on the sensor. The integration time must be sufficiently small so that the image is substantially stationary to avoid causing any motion blur in the captured image.

Figure 2A:
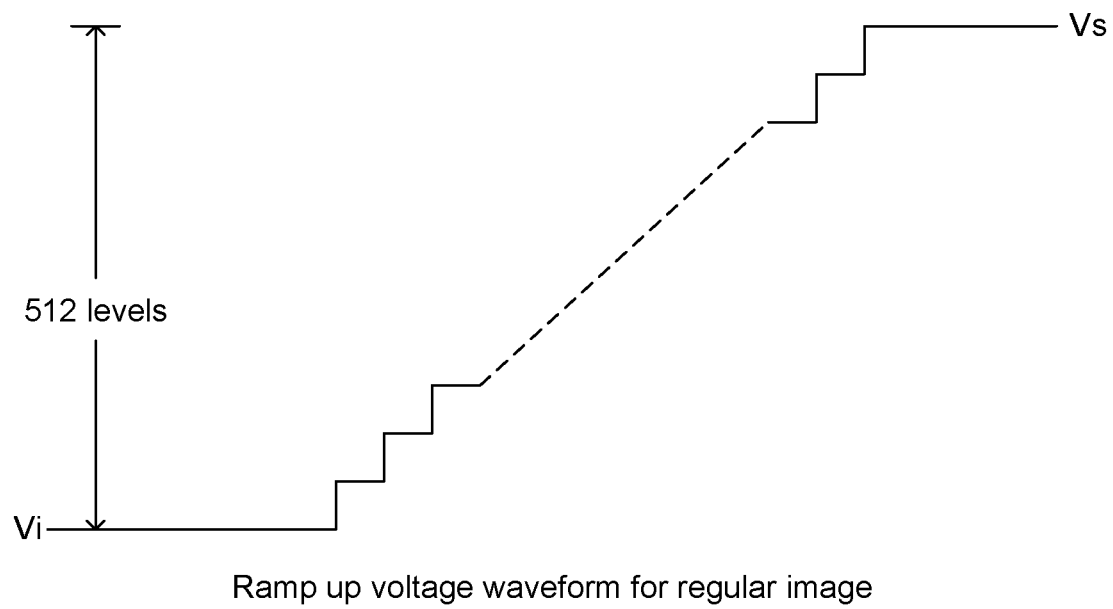
FIGS. 2A-B illustrate ramp voltage waveforms used as a reference signal for the analog-to-digital converter, where the waveforms shown are for 9-bit (FIG. 2A) and 6-bit (FIG. 2B) dynamic resolutions.
Figure 2B:
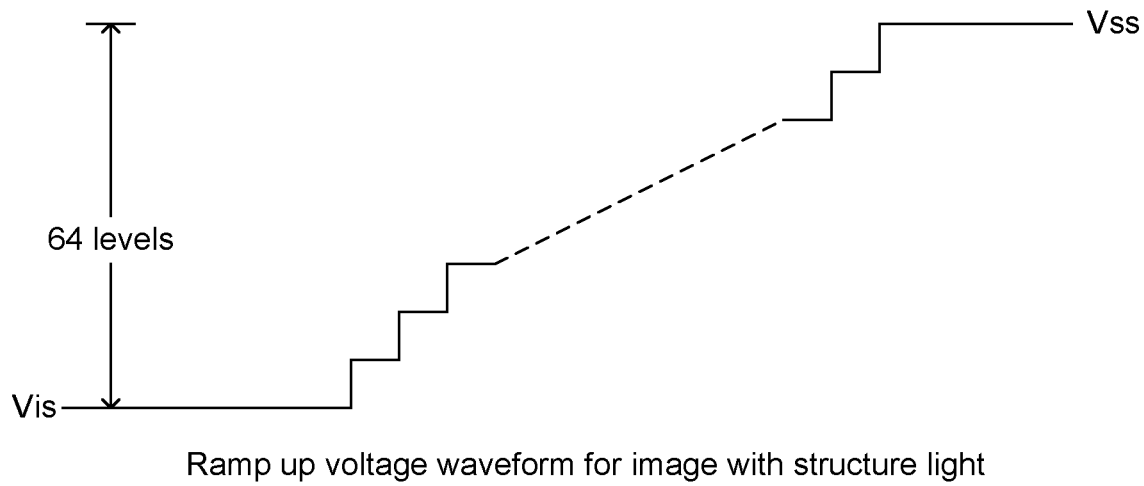

FIG. 1 illustrates an example of ADC (analog-to-digital converter) that can be used for an image sensor. The ADC includes a comparator (110) to compare an input analog signal (120) with a reference signal (130). The analog signal (120) from the analog circuits connected to a pixel is coupled to one terminal of the comparator to compare with a ramp voltage. In one embodiment, the ramp voltage can be generated using a clock that is used for digital logic circuits so that the ramp voltage goes one step higher according to each driving clock. FIG. 2A and FIG. 2B show two examples of ramp voltage corresponding to 9-bit (i.e., 512 levels) and 6-bit (i.e., 64 levels) respectively. The same clock supplied to generate the ramp voltage is also counted by the counter (140). When the ramp voltage level reaches the analog signal (120) from the pixel analog readout circuits connected to a pixel, the comparator output will switch (e.g. from high to low or low to high) to indicate the event. At the same time, the comparator output signal will trigger the registers (150) so as to latch a counter value that counts the number of clocks indicating the ramp voltage value crossing the analog signal (120). The output from the pixel is often measured twice using the correlated double sampling (CDS) technique, which is well known in the field to take care of the fixed pattern noise due to manufacturing variation among pixels. The offset reset signal can be removed using analog circuits (e. g. correlated double sampling) or digital circuits. For digital implementation, the digital counter readout after reset can be subtracted from the digital counter readout of a pixel after an integration period.

There are several factors determining how fast the pixel can accumulate electronic charges and how fast the signal can be readout. As shown in the example of FIG. 1, the analog output signal (120) from analog circuits connected to each pixel is compared to a reference signal (i.e., the voltage ramp). Depending on the desired digital pixel resolution (e.g. 9 bits vs 6 bits), a corresponding ramp signal can be generated. The readout speed will depend on the speed of the counter, the comparator and other related circuits. The ramp signal corresponding to higher digital resolution (i.e., higher dynamic range) will take longer time to generate. The implementation to support 6-bit digital dynamic range as shown in FIG. 2B will be 8 times faster than the implementation for digital 9-bit dynamic range as shown in FIG. 2A.

There are other variations to implement ADC, such as successive approximation ADC. For the successive approximation ADC, the reference voltage starts with a coarse level. Depending on whether the input voltage is higher or lower than the reference voltage, the reference voltage is refined by increasing or decreasing the previous reference voltage by half of a previous voltage interval. The refined reference voltage is used as a current reference voltage for next successive comparison. The process is terminated until a desired resolution is achieved. In each round of successive approximation, one bit is used to indicate whether the input voltage is higher or lower than the reference voltage. Accordingly, the ADC resolution corresponds to the number of successive approximation of the successive-approximation ADC. In general, the higher the dynamic ranges, the longer the readout will be. Not only more comparisons will be required, but also the voltage will take longer time to settle down since the accuracy requirements of the ramp up voltage or reference voltages are high. The sensor array has a large intrinsic RC constant, which takes time to settle to within the limits required by the accuracy. In the case of a high dynamic range, the conductor line carrying the reference voltage (i.e., the ramp reference signal) requires more time to settle due to the inductance, along with R (resistance)

and C (capacitance), of the conductor line. The length of the conductor line for the sensor array usually is in the order of 1,000's μm (micro meter), which may result in an inductance around a few nH (nano Henry). Unlike resistance, the inductance will not be scaled down inversely proportional to the conductor cross section. The high dynamical range is an important factor for image/video quality to provide detailed shades of the objects in the scene. On the other hand, the images for structured light pattern are mainly used to derive depth/shape information based on the geometric information of know patterns, such as grids. The important information to be derived is related to the locations of the grid lines. Accordingly, the requirement on the dynamic range is substantially lower than that for the regular images to be viewed by the human eyes.

Figure 3:
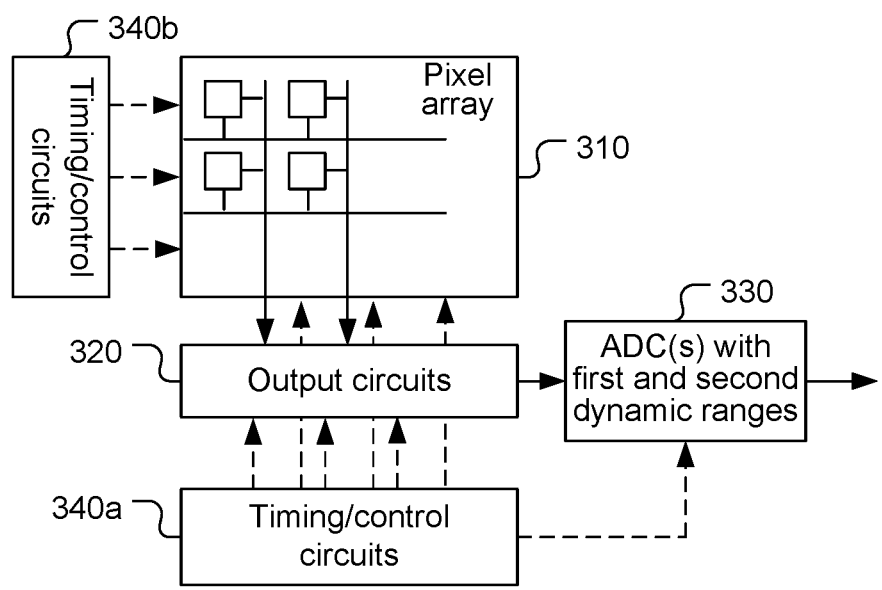
FIG. 3 illustrates an exemplary block diagram of a pixel array for capturing a tandem structured-light image and regular image according to an embodiment of the present invention.

Since the required dynamic range for the structured-light image is much less than that for a regular image, the present invention takes advantage of the different dynamic range requirements to shorten the frame period for the structured-light image. FIG. 3 illustrates a simplified system block diagram of an integrated image sensor incorporating an embodiment of the present invention. The integrated image sensor comprises a pixel array (310) being responsive to light energy received by the pixel array to produce signal data having a voltage level depending on the light energy received, output circuits (320) coupled to the pixel array to access the signal data produced by the pixel array, one or more analog-to-digital converters (ADCs, 330) having a first dynamic range and a second dynamic range, and timing/control circuits (340a and 340b). The pixel array may consist of monochrome pixels or color pixels. The pixel array can be based on the CMOS technology or the CCD technology. The output circuits are coupled to the pixel array under the control of the timing/control circuits. For example, the pixel array outputs can be transferred to the output circuits row by row under the control of the timing/control circuits. The output circuits may also include amplifier and CDS circuit, where the CDS circuit is used to take care of the offset in individual pixels after reset. While the timing/control circuits (340a and 340b) are shown as two separate blocks, they may also be implemented as a unified block.

The ADC circuit(s) is capable of operating at a first dynamic range and a second dynamic range. The first dynamic range is smaller than the second dynamic range. For example, the first dynamic range may correspond to 6 bits and the second dynamic range may correspond to 9 bits. Individual ADCs with different dynamic ranges may be used. Since the structured-light image and the regular image are captured in serial instead of parallel, a single ADC with configurable dynamic range may also be used. For example, an adaptively configurable ADC is disclosed in U.S. Pat. No. 8,369,458 issued to Wong et al. on Feb. 5, 2013. The timing/control circuits may include row scan circuit and column scan circuit. The timing/control circuits are also responsible to generate various control signals such as reset signals. In the following, preferred embodiments are provided regarding configuring the image sensor to capture structured-light images and regular images.

FIG. 4A illustrates an example of the timing for a regular image sensor, where the row timing is shown from frame to frame in the horizontal direction and from the first row (top) to the last row (bottom) in the vertical direction. In a typical image sensor, the image pixels are read out row by row. There are several phases of operation for each row including row reset, integration and readout. The operations usually are staggered from row to row as shown in FIG. 4A. However, the readout operation for a current row has to wait until the previous row readout is complete. For a regular image sensor, the similar timing patterns just repeat from frame to frame with the same frame time. The period time is the same for all frames. FIG. 4A illustrates the general timing diagram for a typical image sensor. The timing charts may not be drawn to scale.

Figure 4B:
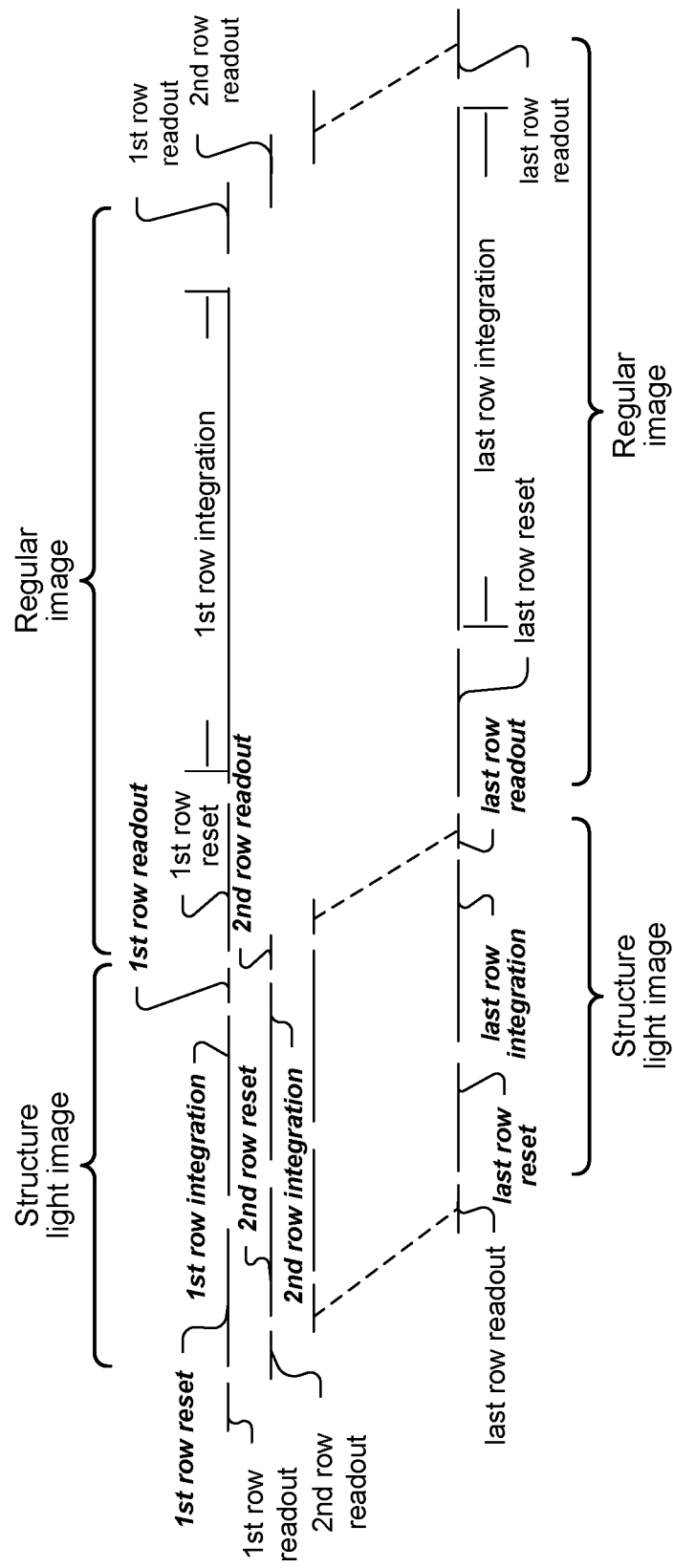
FIG. 4B illustrates an example of a tandem structured-light image and regular image according to an embodiment of the present invention.

FIG. 4B illustrates an example of the timing for capturing a mixed structured-light image and regular image according to one embodiment of the present invention, where the structured light is taken with smaller dynamic range. The frame duration for the structured-light image is much shorter than the frame duration of the following regular image as illustrated in FIG. 4B. The timing charts in FIG. 4B are not drawn to scale, particularly for the structured light section. The section for the structured light has been expanded in order to illustrate more details. In FIG. 4B, the timing signals associated with the structured-light image are shown in Bold-Italic font. The less dynamic range can be achieved, for example, by fewer comparisons with the reference voltage generated by ramping up voltage with a larger step as illustrated in FIGS. 2A and 2B. Alternatively, the reference voltage can be generated with a smaller ramp range between the starting voltage and the ending voltage. Since the readout is faster for this structured-light image than the regular image, the structured-light image could be squeezed within the reset timing period of the regular image. Since the structure light image does not need a dynamic range as high as the regular image, the structure light image reset does not need to be as thorough as that for regular image. Therefore, a shorter reset time could be used for the structured light. Accordingly, in one embodiment, the minimum row reset time among the rows of pixels of the image sensor for the structured-light image can be substantially shorter than the minimum row reset time among the rows of pixels of the image sensor for the regular image.

Figure 5:
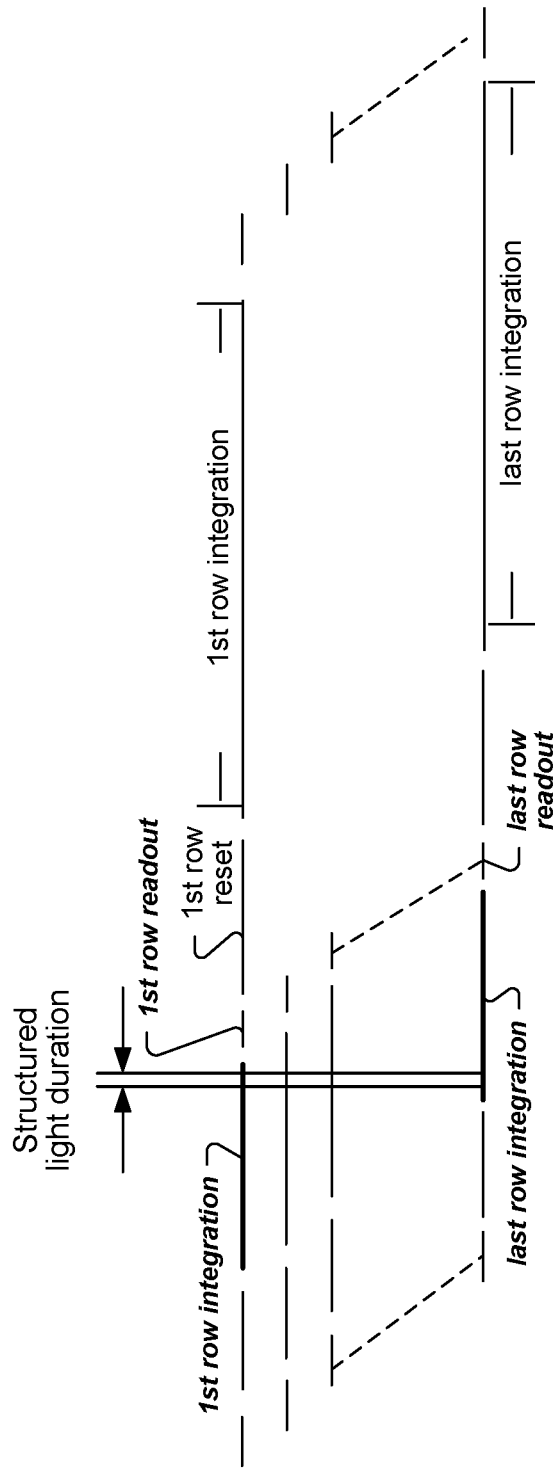
FIG. 5 illustrates an exemplary timing corresponding to FIG. 4B for applying the structured light for capturing a structured-light image according to an embodiment of the present invention, where the structured light duration is explicitly shown and some notations are deleted for clear illustration.

FIG. 5 is identical to FIG. 4B with some notations eliminated to conveniently demonstrate the timing setup. The duration for the structured light is indicated. The structured light duration could be substantially close to the end of first row integration phase for the structured light. On the other hand, the structured light duration must be within the integration phase of the last row for the structured-light image. The optimal structure light pulse duration is from the start of last row integration to the start of first row readout. In order to speed up the operation of capturing a structured-light image, as well as to reduce the impact of the energy of the other light sources, such as ambient light, in the scene entering the camera, the structured light duration is set to be very short. If the integration requires a longer time than desired, the structural light pulse energy can be increased by increasing either the intensity or the duration. In a preferred embodiment, the structured light intensity is substantially stronger compared with the light intensity from the regular light source or ambient light. However, the structured light can be applied for a substantially shorter period than the human visual retention time, making the image of the scene exposed by non-structured light relatively weaker and the signal/noise ratio much stronger for the structure light. The non-structured light may correspond to a broadband, narrowband, or fluoroscopic light. The energy of the structure light pulse may be limited by system power constraints or by a desire not to annoy, distract, or eye-damage persons in the scene exposed to the structured light. Another energy limitation may be a tissue-damage optical-energy threshold in medical-imaging applications. The sensor analog gain may be increased so that the pixel luminance resulting from structured light illumination is well above background noise and luminance from other light sources while the structured light energy is at an acceptably low level. Increased gain results in greater noise amplification and reduced sensor dynamic range.

While the main intended application is for the GI tract, the usage of short-duration and high-intensity structured light can also benefit the non-GI applications. For example, the present invention may also be applied to conventional photography to capture mixed regular images and structured-light images of natural scenes and use the depth or shape information derived from the structured images to render 3D images of the scene. In order to derive more reliable depth or shape information using the structured-light images, it is desirable to select a structured-light source having light spectrum very different from the color spectrum of the underlying scene captured under ambient light or illuminated by one or more non-structured lights.

While there are readout schemes that may start to read the higher (i.e., most significant) bits during integration, the readout with a larger dynamic range will take a longer time to complete the readout. This is due to more comparisons and longer reference voltage settling time needed. Accordingly, reducing the dynamic range for the structured-light image will be able to reduce the row processing duration. This is also true for image sensors operated in the global shutter mode. Accordingly, the settling time associated with a reference voltage, provided to the analog-to-digital converters to compare with an input analog voltage, is shorter for the first structured-light image than for the regular image. Due to the less accuracy required, the reset signal does not need to be held for so long to reset the pixels and/or related circuits to an optimal level.

As shown in FIG. 5, the structured light is preferred to be applied at a specific time so that the duration is short, but the short duration covers at least a portion of integration time for all pixel rows. The control signal to trigger the structured light may be derived from the frame signal and the clock. However, the control signal for the structured light may also come from other module of the integrated sensor. In another implementation, a fixed or programmable delay for the control signal from the sensor can be used to adjust the timings to match optimal system design.

In one embodiment, the structured light is generated using multiple light sources with at least two different colors or patterns. By using multiple colors, a color or a combination of colors can be selected to cause the light spectrum of the selected color(s) substantially different from the color spectrum of associated with regular images of an anticipated scene illuminated by the non-structured light or under ambient light. The spectrum associated with the structured light can be substantially distinct from the spectrum associated with regular images of an anticipated scene. The image sensor may correspond to a color image sensor comprising at least first and second color pixels arranged in a mosaic pattern, and the spectrum associated with the structured light can be substantially concentrated on the spectrum of first or second color pixels. The structured-light image can be captured at reduced spatial resolution by reading out only selected digital outputs related to the first or second pixels having spectrum substantially corresponding to the structured-light spectrum.

For capsule applications, the integrated image sensor may be inside a sealed capsule housing for imaging gastrointestinal tract of human body. Since there is no ambient light in the GI tract, the capsule device has to provide both the structured light and the lighting for regular images. In this case, the structured light sources for structured light images and the illumination light sources for regular images can be sealed in the housing.

Figure 6:
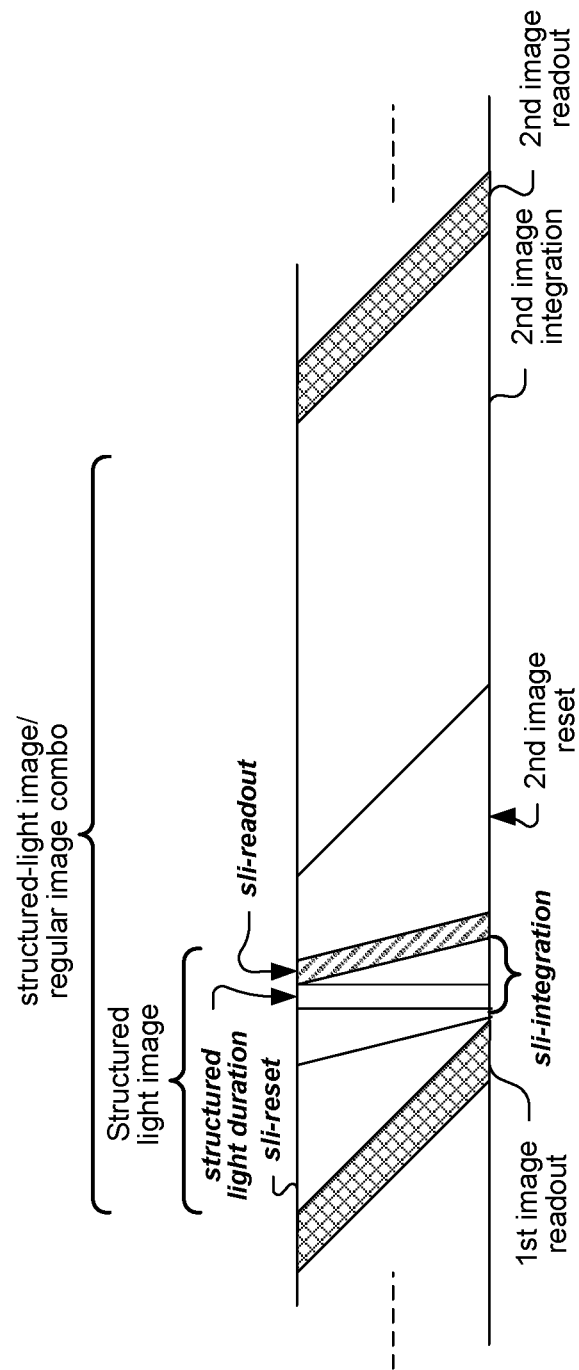
FIG. 6 illustrates another view of applying the structured light for capturing a structured-light image and capturing a regular image according to an embodiment of the present invention.

FIG. 6 illustrates another perspective of the timing charts corresponding to these in FIG. 5, where the image readouts for the structured image and regular images are highlighted using different fill-patterns. The timing signals related to the structured-light image are indicated in FIG. 6, where sli-reset corresponds to the structured-light image reset, sli-integration corresponds to the structured-light image integration and sli-readout corresponds to the structured-light image readout. The structured light duration is also indicated in FIG. 6, where the structured light is applied during the sli-integration. The whole period for capturing the structured-light image may occur during the reset period of a regular image reset. In the example shown in FIG. 6, the reset for the structure light image may be very brief compared to the reset period for a regular image. The timing charts in FIG. 6 illustrate the cycles for capturing a tandem structured-light image and regular image, where the timing for the regular image is modified. In particular, the reset period of the regular image capture is substantially reduced to accommodate the capture of the structured-light image. Accordingly, the timing charts incorporating an embodiment of the present invention shown in FIG. 6 can be considered as two separate images or a combo of structured-light image and timing-modified regular image.

In the embodiments disclosed above, a structured light image is captured temporally close to a regular image so as to provide more accurate depth/shape information for the associated regular image. In another embodiment, a two-session capture is disclosed, where the regular image is split into two sub-images with a structured light image captured in between. The regular integration time for the regular image is split between the two sub-images. The digital outputs for the two regular sub-images are combined to form a regular image output. This approach has several advantages. First, each sub-image is converted into digital outputs using the ADC that is used for the regular image. Accordingly, each sub-image will have the same dynamic range as the regular image of a one-session approach. When the digital outputs of the two sub-images are combined, the final regular image still preserves the full dynamic range. Assume that a pixel with full integration time would get an analog signal to be digitized into 128. By using half the integration time for each session, the pixel will get half the analog signal amount and thus will be digitized to 64. The half integration time is important because integration time may be a substantial component in the total period. Therefore, by using only half the integration time for each session will cause the total time shorter than otherwise.

Figure 7A:
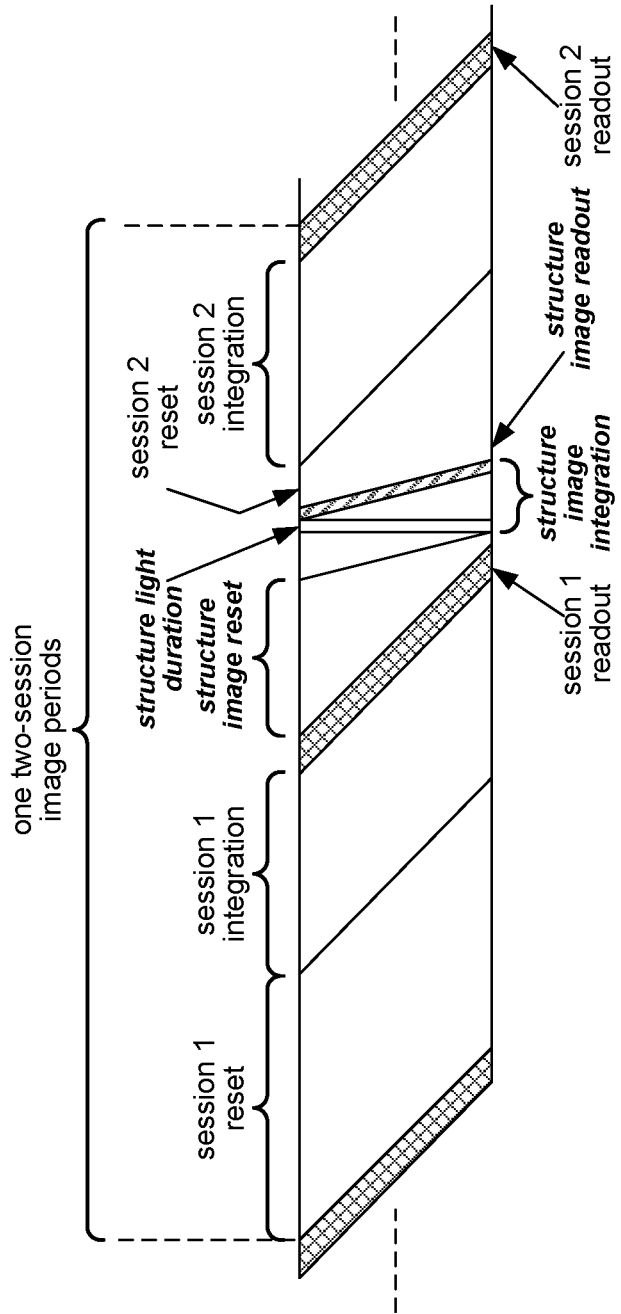
FIG. 7A illustrates exemplary timing charts for capturing a two-session image according to an embodiment of the present invention, where a first regular sub-image is captured in the first session and a mixed image consisting of a structured-light image and a second regular sub-image is captured in the second session, the regular image are combined as the final output and the integration period for the first session is approximately the same as the integration period for the second session.

FIG. 7A illustrates an example of two-session approach according to an embodiment of the present invention. In the first session, a regular image can be captured using regular timing. In the second session, a mixed image is captured, which includes a structured-light image and a timing-modified regular image. The structured-light image is captured between the two session readouts. The first session readout may be temporally stored in a memory or buffer inside the image sensor or outside. When the second session readout is complete, the two readout values from two sessions are combined together. Since the structured-light image is captured between the two sub-images of a regular-scene image, the structured-light image should be very close to the captured regular-scene images temporally. Accordingly, the structured-light image should closely correlate to the regular scene image. The readouts from two sub-images associated with the two sessions are combined into one regular image. In one embodiment, a group of interleaved sub-regular images and structured-light images are taken consecutively. For example, the images in odd numbers are for regular images and images in even numbers are for structured-light images. Images 1 and 3, which are two sub-images, could be combined to form a combined regular image corresponding to image 2, which is a structured-light image. Similarly, images 3 and 5, which are two sub-images, could be combined to form a combined regular image corresponding to image 4, which is a structured-light image. Images 5 and 7 could be combined to form a combined regular image corresponding to image 6, which is a structured-light image. The process can continue with each regular sub-image used twice in general. In this case, the weighting factors for images 1, 3, 5, 7, . . . could be 50/50/50/50 . . . , or it could be 60/40/60/40/60 . . . with the principle of the two combined weighting is 100 percent of the targeted integration time.

Figure 7B:
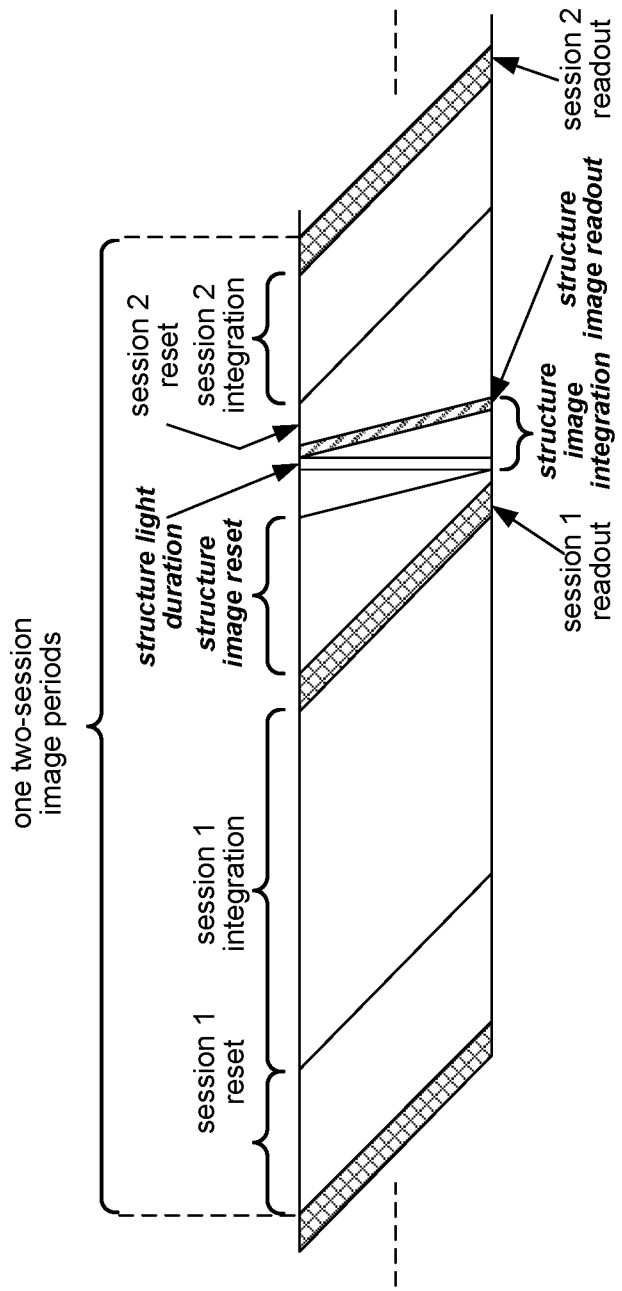
FIG. 7B illustrates exemplary timing charts similar to these of FIG. 7A, where the integration period for the first session is approximately three times as long as the integration period for the second session.

In FIG. 7A, the integration time for the two sub-images is roughly the same. However, the two integration time may also be different. For example, the integration time for the first sub-image may be three times as long as the integration time (also called integration period in this disclosure) for the second sub-image as shown in FIG. 7B. In this case, when the digital outputs from the two sub-images are combined, the combined image has the effect of weighted sum of the first sub-image (i.e., ¾) and the second sub-image (¼). There is no need to perform the weighted sum associated with different integration periods since the weighting will be reflected in the charges accumulated during respective integration periods. The longer integration period results in more accumulated charges, which result in a higher analog signal. Accordingly, the sum of the two digital readouts represents the weighted sum of the two sub-images, where the weighting factors correspond to the integration periods.

In another application of structured-light images, multiple structured light images are used to derive more 3D points than a single structured-light image for one or more associated regular images. For example, multiple structured-light images may be captured consecutively by a capsule camera while traversing in the human gastrointestinal (GI) tract. The regular image can be captured between, before or after the multiple structured-light images. The captured structured-light images can be used to derive a 3D model of the GI tract. This 3D GI tract model can be useful for examining associated regular images of the GI tract.

For two-session regular image capturing with intervening structured-light image, the means for reducing the frame period for the structured-light image as mentioned before can be used. For example, the structured-light image can be captured with a reduced dynamic range of the image sensor compared to the first regular image and the second regular image. The structured-light image may also be captured at lower spatial resolution than the first regular image and the second regular image. Furthermore, the structured-light image can be captured with a reduced image area in a vertical direction, horizontal direction or both compared to the first regular image and the second regular image.

In some cases, the depth or shape information is of interest only for a selected image area. In these cases, the structured-light image can be captured for the selected image area only. Accordingly, it serves an alternative means to reduce the frame period of the structured-light image. The reduced image area may correspond to a reduced image area in the vertical direction, horizontal direction or both compared to the regular image. The means may also be combined with other means, such as reducing the dynamic range or reducing the spatial resolution, for reducing the frame period of the structured-light image.

Reducing the spatial resolution by itself can be used as a technique to reduce the frame period for the structured-light images. For example, the structured-light image can be captured with reduced vertical resolution by only retaining selected rows of pixels and skipping remaining rows of pixels of the image sensor.

For an endoscope application, including a capsule endoscope application, there is no ambient light and the lighting from the endoscope is the only light source. Therefore, the integration time of each row needs not to be the same as long as the duration of the light exposure is the same for every line. For the endoscope environment, the lower dynamic range of structured-light image than that of the regular image also benefits from temporal proximity between the structured-light image and the regular image. Therefore, the structured-light image according to the present invention should bear more accurate depth or shape information correlated with the regular image.

For power sensitive applications such as the capsule endoscope and wearable device, less dynamic range also saves power due to less comparison operations and shorter integration time, which requires less structured light energy. On the other hand, since signal to noise ratio is not so important to structured-light image, its gain can be set to substantial higher to further save energy.

A camera system usually includes an exposure control function to control the operating parameters of the image sensor so that the overall intensity of the image taken is at the right level within certain range conducive for viewing. The image intensity is derived from the pixel intensity. The detailed control often is subject to the preference of camera system designer. For example, the image intensity is determined by the average of pixel intensity of central portions of the image. In another example, the mean of the pixel intensity of the central portion is used as the image intensity. In another example, multiple areas of the image are used instead of the central portion. If the intensity is found to be too high, then the gain or the integration time can be reduced. If the intensity is too low then the gain or the integration time can be increased. Furthermore, the amount of adjustment from one image to the next can be dependent on how much the intensity is deviated from the preferred level or range.

A camera system may also provide the lighting to augment the ambient light. The lighting from the camera system may also be the sole lighting source, such as a regular endoscope or a capsule endoscope. For a camera used for pipe examination or for deep sea exploration, the lighting from the camera is also the sole lighting source. In such a system, the exposure control will control the gain, integration time, lighting intensity and/or energy or a combination of them. If an image has too strong intensity, the value of (gain×integration×light energy) will be reduced for the subsequent image or images. On the other hand, if an image has too weak intensity, the value of (gain×integration×light energy) will be increased for the subsequent image or images. The amount of adjustment from one image to the next may dependent on much the intensity is deviated from the preferred level or range.

An embodiment of the present invention addresses dual exposure controls for capturing structured-light images and regular images using a single image sensor. Based on this embodiment, there are two exposure control loops for the same image sensor, one for the structured-light image and the other for the regular image. In the case that the regular image lighting is substantially dependent on the light controlled by the camera system (e.g. negligible or no ambient light), the exposure condition is very similar for both structured light and the regular light since the distance to the scene is practically the same for both cases. Accordingly, one exposure control loop could be used and the other exposure control is dependent on the first exposure control loop. For example, (gain×integration×light energy) of structure light can be linearly dependent on (gain×integration×light energy) of regular light image or vice versa. In another embodiment, other dependence is used. For example, gamma-type dependence or dependence on the intensity distribution may also be used.

Figure 8:
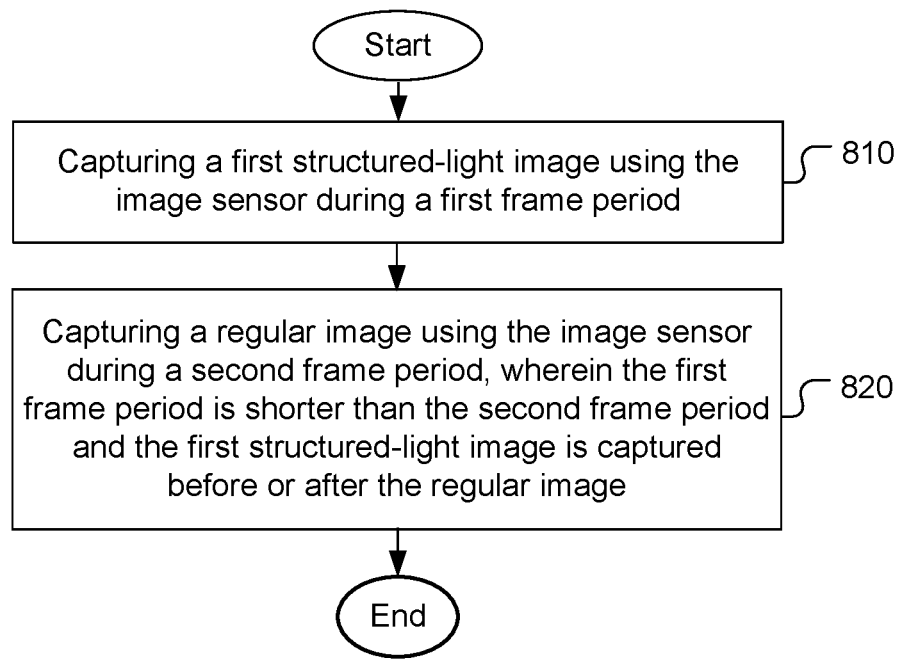
FIG. 8 illustrates an exemplary flowchart for capturing a tandem structured-light image and regular image according to an embodiment of the present invention, where the structured-light image has lower dynamic range than the regular image.

In the case where there is ambient light, the structured-light needs to be sufficiently strong to cause the structure light pattern more discernable in the structured-light image for analysis. In this case, the light intensity in the above analysis is composed of ambient light and light or lights projected to the scene controlled by the exposure control of the camera system. In this case, there might be no need for camera control to project light for regular image if ambient light is sufficient. However the structured light has another constraint that the projected structured-light must be strong enough to show its pattern and/or color in the structured-light image. If the spectrum of the structured light is substantially concentrated in the spectrum of one particular color of the image sensor, the intensity of that particular color of the structured light image and/or the overall intensity are considered. In one embodiment, if structured-light sources are capable of generating multiple colors, then the intensity of each color component in the regular image is considered. The structured light source color corresponding to the weaker color in the regular image is chosen in order to make the structured color stand out or to have a higher signal to background ratio statistically for easy analysis FIG. 8 illustrates an exemplary flowchart for capturing a mixed structured-light image and regular image according to an embodiment of the present invention. Capturing a first structured-light image using the image sensor during a first frame period in step 810. A regular image is captured using the image sensor during a second frame period, where the first frame period is shorter than the second frame period and the first structured-light image is captured before or after the regular image in step 820.

Figure 9:
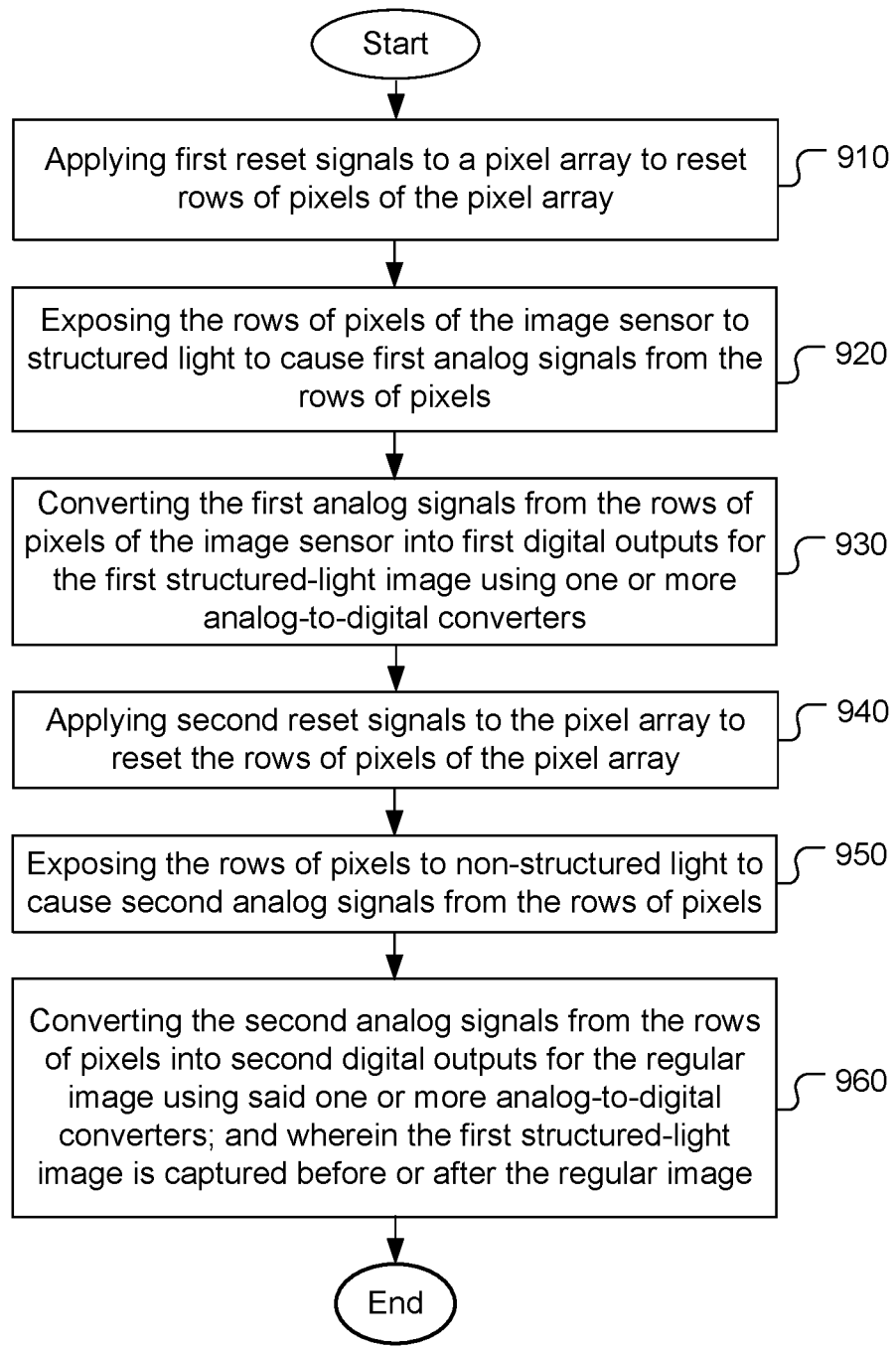
FIG. 9 illustrates an exemplary flowchart for capturing a tandem structured-light image and regular image according to another embodiment of the present invention, where the structured-light image has lower dynamic range than the regular image.

FIG. 9 illustrates an exemplary flowchart for capturing a tandem structured-light image and regular image according to one embodiment of the present invention, where the structured-light image has lower dynamic range than the regular image. First reset signals are applied to a pixel array to reset rows of pixels of the pixel array in step 910. The rows of pixels of the image sensor are exposed to structured light to cause first analog signals from the rows of pixels in step 920. The first analog signals from the rows of pixels of the image sensor are converted into first digital outputs for the first structured-light image using one or more analog-to-digital converters in step 930. Second reset signals are applied to the pixel array to reset the rows of pixels of the pixel array in step 940. The rows of pixels are exposed to non-structured light to cause second analog signals from the rows of pixels in step 950. The second analog signals from the rows of pixels are converted into second digital outputs for the regular image using said one or more analog-to-digital converters in step 960. The first structured-light image is captured before or after the regular image in step 960, where the first dynamic range is smaller than the second dynamic range.

The invention may be embodied in other specific forms without departing from its spirit or essential characteristics. The described examples are to be considered in all respects only as illustrative and not restrictive. Therefore, the scope of the invention is indicated by the appended claims rather than by the foregoing description. All changes which come within the meaning and range of equivalency of the claims are to be embraced within their scope.

The invention claimed is:

1. An integrated image sensor, comprising:
a pixel array being responsive to light energy received by the pixel array to produce pixel signals having a voltage level depending on the light energy received by the pixel array;
one or more output circuits coupled to the pixel array to access the pixel signals produced by the pixel array;
one or more analog-to-digital converters having a first dynamic range and a second dynamic range;
one or more timing and control circuits coupled to the pixel array, said one or more output circuits, said one or more analog-to-digital converters or a combination thereof, wherein said one or more timing and control circuits are arranged to:
capture, by the pixel array, a structured-light image formed on a common image plane during a first frame period by applying first reset signals to the pixel array to reset rows of pixels of the pixel array, exposing the rows of pixels of the pixel array to first illumination from a structured light source to cause first analog signals from the rows of pixels and converting the first analog signals from the rows of pixels of the pixel array into first digital outputs for the structured-light image using one or more analog-to-digital converters;
capture, by the pixel array, a first regular image formed on the common image plane during a second frame period by applying second reset signals to the pixel array to reset the rows of pixels of the pixel array, exposing the rows of pixels to second illumination from a non-structured light source to cause second analog signals from the rows of pixels, and converting the second analog signals from the rows of pixels into second digital outputs for the first regular image using said one or more analog-to-digital converters;
capture, by the pixel array, a second regular image formed on the common image plane during a third frame period by applying third reset signals to the pixel array to reset the rows of pixels of the pixel array, exposing the rows of pixels to the second illumination from the non-structured light source to cause third analog signals from the rows of pixels, and converting the third analog signals from the rows of pixels into third digital outputs for the second regular image using said one or more analog-to-digital converters;
combine the second digital outputs and the third digital outputs to form a combined regular image; and
wherein the structured-light image is captured between the first regular image and the second regular image to derive depth or shape information for the combined regular image.

2. The integrated image sensor of claim 1, wherein said one or more analog-to-digital converters correspond to a configurable analog-to-digital converter to provide both the first dynamic range and the second dynamic range.

3. The integrated image sensor of claim 1, wherein said one or more analog-to-digital converters correspond to two analog-to-digital converters with two different resolutions to provide both the first dynamic range and the second dynamic range.

4. The integrated image sensor of claim 1, wherein said one or more timing and control circuits are further arranged to cause the structured-light image to be captured at lower spatial resolution than the first regular image and the second regular image.

5. A camera system, comprising:
a structured light source;
a non-structured light source; and
an integrated image sensor, comprising:
  a pixel array being responsive to light energy received by the pixel array to produce pixel signals having a voltage level depending on the light energy received by the pixel array;
  one or more output circuits coupled to the pixel array to access the pixel signals produced by the pixel array;
  one or more analog-to-digital converters having a first dynamic range and a second dynamic range;
  one or more timing and control circuits coupled to the pixel array, said one or more output circuits, said one or more analog-to-digital converters or a combination thereof, wherein said one or more timing and control circuits are arranged to:
  capture, by the pixel array, a structured-light image formed on a common image plane during a first frame period by applying first reset signals to the pixel array to reset rows of pixels of the pixel array, exposing the rows of pixels of the pixel array to first illumination from the structured light source to cause first analog signals from the rows of pixels and converting the first analog signals from the rows of pixels of the pixel array into first digital outputs for the structured-light image using one or more analog-to-digital converters;
  capture, by the pixel array, a first regular image formed on the common image plane during a second frame period by applying second reset signals to the pixel array to reset the rows of pixels of the pixel array, exposing the rows of pixels to second illumination from the non-structured light source to cause second analog signals from the rows of pixels, and converting the second analog signals from the rows of pixels into second digital outputs for the first regular image using said one or more analog-to-digital converters;
  capture, by the pixel array, a second regular image formed on the common image plane during a third frame period by applying third reset signals to the pixel array to reset the rows of pixels of the pixel array, exposing the rows of pixels to the second illumination from the non-structured light source to cause third analog signals from the rows of pixels, and converting the third analog signals from the rows of pixels into third digital outputs for the second regular image using said one or more analog-to-digital converters;
  combine the second digital outputs and the third digital outputs to form a combined regular image; and
  wherein the structured-light image is captured between the first regular image and the second regular image to derive depth or shape information for the combined regular image.

6. The camera system of claim 5, wherein the first frame period is shorter than a sum of the second frame period and the third frame period.

7. The camera system of claim 5, wherein the structured-light image is captured at lower spatial resolution than the first regular image and the second regular image.

8. The camera system of claim 5, wherein said one or more analog-to-digital converters correspond to a configurable analog-to-digital converter to provide both the first dynamic range and the second dynamic range.

9. The camera system of claim 5, wherein said one or more analog-to-digital converters correspond to two analog-to-digital converters with two different resolutions to provide both the first dynamic range and the second dynamic range.

10. An endoscope for in vivo viewing of human gastrointestinal (GI) tract, comprising:
a structured light source;
a non-structured light source;
an integrated image sensor, comprising:
  a pixel array being responsive to light energy received by the pixel array to produce pixel signals having a voltage level depending on the light energy received by the pixel array;
  one or more output circuits coupled to the pixel array to access the pixel signals produced by the pixel array;
  one or more analog-to-digital converters having a first dynamic range and a second dynamic range;
  one or more timing and control circuits coupled to the pixel array, said one or more output circuits, said one or more analog-to-digital converters or a combination thereof, wherein said one or more timing and control circuits are arranged to:
  capture, by the pixel array, a structured-light image formed on a common image plane during a first frame period by applying first reset signals to the pixel array to reset rows of pixels of the pixel array, exposing the rows of pixels of the pixel array to first illumination from the structured light source to cause first analog signals from the rows of pixels and converting the first analog signals from the rows of pixels of the pixel array into first digital outputs for the structured-light image using one or more analog-to-digital converters;
  capture, by the pixel array, a first regular image formed on the common image plane during a second frame period by applying second reset signals to the pixel array to reset the rows of pixels of the pixel array, exposing the rows of pixels to second illumination from the non-structured light source to cause second analog signals from the rows of pixels, and converting the second analog signals from the rows of pixels into second digital outputs for the first regular image using said one or more analog-to-digital converters;
  capture, by the pixel array, a second regular image formed on the common image plane during a third frame period by applying third reset signals to the pixel array to reset the rows of pixels of the pixel array, exposing the rows of pixels to the second illumination from the non-structured light source to cause third analog signals from the rows of pixels, and converting the third analog signals from the rows of pixels into third digital outputs for the second regular image using said one or more analog-to-digital converters;
  combine the second digital outputs and the third digital outputs to form a combined regular image; and wherein the structured-light image is captured between the first regular image and the second regular image to derive depth or shape information for the combined regular image.

11. The endoscope of claim 10, wherein the structured-light image is captured at lower spatial resolution than the first regular image and the second regular image.

12. The endoscope of claim 10, wherein said one or more analog-to-digital converters correspond to a configurable analog-to-digital converter to provide both the first dynamic range and the second dynamic range.

13. The endoscope of claim 10, wherein said one or more analog-to-digital converters correspond to two analog-to-digital converters with two different resolution to provide both the first dynamic range and the second dynamic range.

14. The endoscope of claim 10 further comprising a capsule housing adapted to be swallowed, wherein the pixel array, the structured light source, the non-structured light source, said one or more output circuits, and said one or more timing and control circuits are enclosed and sealed in the capsule housing.

\* \* \* \* \*